United States Patent
Buffle et al.

[11] Patent Number: 5,865,972
[45] Date of Patent: Feb. 2, 1999

[54] INTEGRATED ELECTROCHEMICAL MICROSENSORS AND MICROSYSTEMS FOR DIRECT RELIABLE CHEMICAL ANALYSIS OF COMPOUNDS IN COMPLEX AQUEOUS SOLUTIONS

[75] Inventors: Jacques Buffle, Certoux; Mary-Lou Tercier, Genève, both of Switzerland; Cécile Belmont, Ugine, France; Milena Koudelka-Hep, Neuchâtel; Giovanni Carlo Fiaccabrino, Cortaillod, both of Switzerland

[73] Assignee: Université de Geneve, Geneva, Switzerland

[21] Appl. No.: 762,342

[22] Filed: Dec. 9, 1996

[30] Foreign Application Priority Data

Dec. 19, 1995 [FR] France ................... 95 15071

[51] Int. Cl.$^6$ .................................. G01N 27/26
[52] U.S. Cl. .................. 204/412; 204/413; 204/415; 204/416; 204/434
[58] Field of Search .................. 204/403, 416, 204/418, 419, 415, 412, 434, 413

[56] References Cited

U.S. PATENT DOCUMENTS

| | | | |
|---|---|---|---|
| 3,912,614 | 10/1975 | Spracklen et al. | 204/415 |
| 4,272,328 | 6/1981 | Kim et al. | 204/418 |
| 5,320,735 | 6/1994 | Kato et al. | 204/419 |
| 5,378,343 | 1/1995 | Kounaves et al. | 204/413 |
| 5,378,383 | 1/1995 | Jachow et al. | 252/62.56 |

FOREIGN PATENT DOCUMENTS

| | | |
|---|---|---|
| 2 346 716 | 10/1977 | France. |
| 2 360 074 | 2/1978 | France. |

OTHER PUBLICATIONS

Analytical Chemistry vol. 66, No. 3, 1 Feb. 1994, pp. 418–423.
S.P. Kounaves: "Iridium–based Ultramicroelectrode Array Fabricated by Microlithography" Patent Abstracts of Japan vol. 12, No. 278 (P–738), 1 Aug. 1988 & JP–A–63 058149. (Matsushita Electric Ind. Co.), 12 Mar. 1988.
Sensors and Actuators, B. Chemical, vol. B21, No. 1, Jul. 1994, Lausanne, CH pp. 33–37, XP000479669.

*Primary Examiner*—T. Tung
*Attorney, Agent, or Firm*—Griffin, Butler, Whisenhut & Kurtossy

[57] ABSTRACT

A microsensor for electrochemical measurements allowing the determination of concentration or concentration profile of at least one chemical compound with small size or molecular weight, under organic, inorganic, neutral or ionic form in an aqueous environment. The microsensor comprises an array (15) of microelectrodes (16), assembled on a chip (10) supported by an isolating substrate (7), and linked with at least one conductor protected by an insulating layer to a contact allowing the connection to a measuring apparatus. The said microsensor is totally coated with an hydrophilic gel (25) which is chemically inert with respect to the chemical compound, is hydrated at a level of at least 70 %, and has a thickness superior to 10 times the size of the microelectrodes (16). And an integrated electrochemical microsystem including the microsensor.

20 Claims, 5 Drawing Sheets

INTEGRATED ELECTROCHEMICAL MICROSENSORS AND MICROSYSTEMS FOR DIRECT RELIABLE CHEMICAL ANALYSIS OF COMPOUNDS IN COMPLEX AQUEOUS SOLUTIONS

BACKGROUND OF THE INVENTION

1. Field of the Invention

The object of the present invention is a gel based electroanalytical microsensor and an integrated microsystem allowing reliable measurement of concentration for a variety of chemical compounds and ions in complex aqueous environment, avoiding interferences from other compounds present in the environment and allowing to distinguish between the different chemical forms of the compound of interest.

2. Background Art

Concentration of compounds in solution have long been determined by use of well-known electrodes combined with electrochemical and particularly dynamic electroanalytical techniques based on oxido-reduction processes. These techniques consist of recording current / potential curves, in other word functions F(U, I), under different experimental conditions. In voltammetric, polarographic and chronoamperometric techniques, the potential is swept as a function of time between two extreme values, and the resulting current is measured. In potentiometric techniques, the current is swept and the potential is recorded. In the present invention all these techniques can be used with the microsensor and the integrated microsystem, but for convenience for the rest of this description, only the term "voltammetry" will be used to represent the whole of these techniques. A variety of function F(U, I) have been proposed to carry out measurements in a large range of concentration and in particular to increase the sensitivity and the selectivity towards a given compound. The most commonly used voltammetric techniques are mentioned below. They allow the measurement of concentrations between $10^{-11}$ and $10^{-4}$M ($10^{-9}$ and $10^{-2}$ g/l), and they can be classified into the three following groups illustrated with non-restrictive examples.

i) Techniques without preconcentration of the test compound (analyte): Cyclic Voltammetry-CV.
ii) Techniques with electrochemical preconcentration of the compound on the sensor: Anodic Stripping Voltammetry-ASV; Square Wave Anodic Stripping Voltammetry-SWASV.
iii) Techniques with chemical preconcentration of the compound on the sensor: Adsorptive Cathodic Stripping Voltammetry-AdCSV.

In particular the techniques from the last two groups allow the detection of a large number of compounds at trace levels, as low as $10^{-11}$M (in the order of 0.001 $\mu$g/dm$^3$). The said compounds can be organic or inorganic compounds under neutral, anionic or cationic form, such as metallic cations.

The electrodes traditionally used are usually made of gold, platinum or carbon and very often of mercury which presents the great advantage of surface reproducibility.

In "An Iridium based Mercury Film Electrode, part I, Selection of Substrate and Preparation" by S. P. Kounaves and J. Buffle (J. Electronal. Chem., 216, 53–69 (1987) Ref. 1), the authors showed that iridium is preferable to any other metal because of its high resistance to oxidation by oxygen, its low solubility in mercury and because of the good mercury-iridium cohesion. It is therefore possible to deposit mercury on the iridium, so that the electrode can be used either as an iridium electrode (without mercury), or as a mercury electrode, which extends its field of application. Classical electrodes can be found with various geometry and mechanical configurations (disc electrodes, rotating disc, hanging or dropping mercury drops, mercury film...). Their dimensions are often in the range 0.1 mm to 10 mm. It is known that microelectrodes with dimensions less than 20 $\mu$m present several advantages, such as the ability to work in quiescent or in highly resistive environments, as well as enhanced stability for the mercury films. The fabrication of mercury-plated iridium-based microelectrodes has been described in "A Mercury plated Iridium based microelectrode: preparation and some properties" by R. R. Vitre, M. L. Tercier, M. Tsacopoulos and J. Buffle (Anal. Chem. Acta 249, 419–425 (1991) Ref. 2).

Further improvements have been made in the fabrication procedure. For example S. P. Kounaves et al (patent U.S. Pat. No. 5, 378, 343, Ref. 3) used microtechnology for the fabrication of a microelectrode based sensor. In this patent, the working electrode is always made of mercury and is in direct contact with the aqueous solution to analyse.

Recently in "Fabrication and characterisation of mercury-plated iridium microelectrode arrays" by G. C. Fiaccabrino, M. L. Tercier, J. Buffle, N. de Rooij, M. Koudelpa-Hep (Transducers 95, Digest of Technical papers, vol. 2, 478 (1995), Ref. 4), the authors describe a fabrication procedure involving thin film technology and photolithography allowing the fabrication of a sensor analogous to the previous one, but with increased sensitivity and reliability.

Each single voltammetric technique allows to determine simultaneously the concentration of several compounds without modifying the solution where the measure is carried out. A given sensor allows thus to detect and to quantify a large number of organic or inorganic chemical compounds, which makes these techniques particularly useful for the chemical analysis of complex aqueous solutions of biological, industrial or environmental origins. These measurements can be carried out either after sampling, for example in a drop of blood, or directly in situ, for example in lake or sea waters and in sediments, by means of a probe including the sensor, or on line for example as detectors in separative chromatographic techniques or in flow injection analysis.

At present a number of difficulties limit the use of these techniques in complex environments. For routine analysis, it is necessary to make repetitive, accurate and reliable measurements over a long period of time, and the sensor should be able to work in hostile media and environment. The term "hostile media" includes solution to analyse containing compounds that we do not wish to detect but that can interfere with the measurement in a way or another by modifying the physicochemical conditions at the electrode surface, and in consequence the voltammetric signal. An example of this type of interference (interference 1) concerns compounds that are oxidised or reduced at the electrode surface with the compound to analyse and where oxidoreduction products react with the analyte. This is the case in particular with oxygen which is present in most of the solutions. Its reduction causes an increase of pH close to the electrode surface and eventually the precipitation of metal ions to analyse, as metal hydroxides. Another type of interference (interference 2) concerns macromolecules, colloids and other surface-active compounds which can adsorb at the electrode surface, and block or modify the electron transfer between the electrode and the compound to analyse. A third type of interference (interference 3) concerns contaminations, i. e. the release of ions to analyse, by the system itself. The term "hostile environment" includes the use of the microsensor in probes placed in situ in extreme conditions (bottom of oceans, sinking wells, industrial chemical reactors).

An additional limitation for the current sensors is the influence of the hydrodynamic flux or the stirring, on the measured signal. In particular for in situ measurements, where stirring is uncontrolled and can vary with time, this can lead to irreproducible results over long periods of time.

Finally, for the complex environments previously mentioned and particularly for metal ions, the compound to analyse is often present under different chemical forms (complexed or not, under various redox states, adsorbed or not on particles in suspension. . . ). For a correct analytical interpretation, the sensor should be capable of discriminating between the different forms.

In the presently known voltammetric sensors or electrochemical systems, the electrodes are directly in contact with the analytical environment. Such sensors or systems are not capable of solving the above mentioned problems.

One of the solutions used to solve the unreliability associated with the interferences of type 1 and 2 consists of drastically pretreating the samples by physical, chemical or biological means, which can eliminate the interferences (strong acids or oxidising agents, enzymatic attack. . . ). Such procedures have several disadvantages: large quantities of solvent are needed, they are time consuming, difficult if not impossible to use for in situ measurements, and errors can be generated for example by contaminations or loss by adsorption of the compound to analyse, from or on the pretreatment system.

Furthermore after a pretreatment, it is no longer possible to discriminate between the different chemical forms of the compounds to analyse, although it is often essential to know their relative content to solve industrial, medical or environmental problems.

The interfering compounds of type 2, which are the most frequently encountered in natural waters, biological and industrial fluids, are organic or inorganic colloidal substances or compounds with relatively high molecular mass, such as humic or fulvic compounds (vegetal decomposition products) present in soils and waters, as well as proteins or polysaccharides. Microporous membranes, for example made of Nafion or cellulose acetate have been proposed to protect the surface of the electrode. The efficiency and/or the reliability of preparation have shown to be poor and insufficient for voltammetric sensors which should be used in situ for long periods of time. Also in some cases, they cannot be used because they react with the test compounds.

None of the known techniques allow to satisfactorily protect the electrodes against hydrodynamic flow variations or stirring of the environment to analyse. In particular, reducing the size of the electrode is insufficient in itself to avoid hydrodynamic effects. Indeed these effects are negligible only for microelectrodes with size less than 0.2 $\mu$m, whereas the smallest dimensions that can be obtained by the known photolithographic techniques are larger then 0.5 $\mu$m. In this conditions, variations in the analytical signal of the order of 30 to 50% can be observed due to the influence of the hydrodynamic flow in the test solution.

Some limitations in the reproducibility of the measurements carried out with the prior art voltammetric sensors results from the said sensors fabrication itself. In particular limiting factors are the surface conditions of the deposited iridium film (which influences the cohesion of the mercury film on iridium), and the renewing conditions of the mercury films on the iridium. Indeed although a given film can be used for continuous measurements for at least several days, it must be renewed after this period of time. Adequate conditions must be used for this operation to avoid the formation of mercuric oxides at the surface of the electrode, leading to irreproducibility of the sensor. These aspects are not mentioned in the prior art patents (Ref. 3).

The present invention provides a sensor and an integrated electrochemical microsystem providing the appropriate conditions to avoid the corresponding problems. Anyway, it must be noticed that the absence of protection on the prior art voltammetric sensor is responsible for their fragility and their sensitivity to external conditions. The physical protection of the electrodes by the gel disclosed in the present invention greatly improves the long term stability of the sensors.

SUMMARY OF THE INVENTION

An object of the present invention is to obviate the above mentioned disadvantages encountered with the prior art electrochemical sensors by providing: i) a new microsensor, ii) an ensemble of microsensors and iii) a reliable and robust integrated electrochemical microsystem capable of measuring without contaminations and over long periods of time the concentration of organic and inorganic compounds, notably at trace levels, and discriminating their different chemical forms in complex aqueous systems containing substances susceptible of perturbing the analytical signal.

Another object of the present invention is to provide a microsensor for electrochemical measurements allowing the determination in an aqueous environment of concentration or concentration profile of at least one chemical compound with small size or molecular weight under organic, inorganic, neutral or ionic form. The said microsensor comprises an array of microelectrodes, assembled onto a chip supported by an isolating substrate, and linked with at least one conductor protected by an insulating layer to a contact allowing the connection to a measuring apparatus. The said microsensor is totally coated with.an hydrophilic gel which is chemically inert with respect to the test chemical compound, is hydrated at a level of at least 70%, and has a thickness larger than 10 times the size of the microelectrodes.

The microelectrodes can be all interconnected and thus form a single so called "simple" microsensor. In contrast microelectrodes or groups of microelectrodes can be electrically isolated from each other to be separately addressable and hence form an ensemble of electrochemical microsensors. The microsensors (simple or as part of an ensemble) are used in association with at least one reference electrode and eventually with an auxiliary electrode, such as the usual commercially available electrodes.

In a preferred embodiment, the simple microsensor or the ensemble of microsensors, the reference electrode and eventually the auxiliary electrode are assembled on a single isolated substrate to form an integrated electrochemical microsystem.

In a preferred embodiment, the simple microsensor or the ensemble of microsensors is formed by an array of microelectrodes with variable geometry and distribution, the said microelectrodes may be interconnected or not and have small size. For example disc microelectrodes of diameter 0.5 to 30 $\mu$m can be used. However other geometries are possible. The microelectrodes are either constituted of iridium or iridium covered with a mercury layer, or both. Iridium allows the detection and the quantification of chemical species with oxidoreduction potential comprised between 0 and 1.5 V with respect to Ag/AgCl 1M, such as $O_2$, Hg(II), As(III) or Se(VI). Mercury drop microelectrodes allow the detection and the quantification of chemical species with oxidoreduction potential comprised between −1.5 and 0 V with respect to Ag/AgCl 1M, such as $IO_3^-$, S(-II), Fe(II), Mn(II), Zn(II), Cd(II), Pb(II), Tl(I) or Bi(III).

In an integrated electrochemical microsystems, supporting on a single board, a simple microsensor or an ensemble of microsensors, a reference electrode and eventually a counter electrode, the reference electrode can be of $Ir/IrO_2$ type and the counter electrode can be made of iridium, but other materials can be chosen. For such a sensor, the fabrication of the microelectrode array can be done using the thin film technology and photolithography as indicated for instance by Kounaves et al and Fiaccabrino et al (Ref. 3 and 4).

To fulfil the requirements of sensor robustness and lifetime, the gel must possess a high mechanical resistivity, a long term stability with regards to chemical, enzymatic and micro-biological actions, a swelling independent of the physicochemical properties of the aqueous environment, such as the pH, the temperature and ionic strength. Furthermore, the gel porosity must be large enough to allow normal or little hindered diffusion of the test compound, but also low enough to retain interfering macromolecular or colloidal compounds. The preferred gel should not contain any neutral or charged compound with complexing properties for the test compound. In contrast, it is desirable that the chemical structure of the gel contain chemical groups such as alcoholic groups, which can fix additional constituents allowing to maintain the optimal physicochemical conditions in the gel (acid-base, redox. . . ), for the measurement of the compound to analyse. In particular it is very useful to fix pH buffering agents in the gel to avoid pH variations during the measurement, for example when oxygen is reduced at the electrode surface.

Gels showing the above characteristics can be obtained from compounds, such as cellulose or derived cellulose, reticulated dextrans, purified agarose with low content of sulphate or carboxyl groups, reticulated agarose, polyacrylamide, polyacrylamide and agarose polymers, and hydroxyalkylmethacrylates such as hydroxyethylmethacrylate (HEMA).

The compounds or compositions allowing to confer acid-base buffer properties to the gel are well known. For a pH to be fixed between 5 and 9, the buffers MES (morpholinoethane sulfonic acid), PIPES (piperazine Bis-N, $N^1$-2-ethane sulfonic acid), cholamine chloride, HEPES(N-(2hydroxyethyl)-piperazine-$N^1$-2 ethane sulfonic acid), HEPPS(N-(2-hydroxyethyl)-piperazine-$N^1$-3 propane sulfonic acid), HEPPSO(N-(2hydroxyethyl)-piperazine-$N^1$-2 propane sulfonic acid), MOPS (morpholinopropane sulfonic acid) and MOPSP (3-N-(morpholino)-2-hydroxy propane sulfonic acid) can be chosen. Depending on the buffer chemical nature, the fixation in the gel can be obtained as previously mentioned by forming covalent bond. This fixation is also possible by direct retention of the buffer compound in the gel, by physical adsorption, by hydrogen bonding or indirectly by adsorption of the buffer compound on large particles, which are retain in the gel because of their large size. In this case, the particles must be inert with the compound to analyse, and can be for example, agarose or silica beads.

As previously indicated, the thickness of the gel on the microsensor may depend on microelectrode size (the diameter of the electrode is in the range 0.5 to 30 μm). Two limiting conditions fix the extreme values for the gel thickness. It must be small enough to allow a rapid equilibration of the compound of interest by diffusion between the solution and the gel. Experience shows that for that purpose the thickness should be less than a few mm, in preference 1–2 mm. On the other side, the gel thickness should be sufficiently large with respect to each microelectrode, to avoid variation of the average concentration in the gel, due to diffusion of the test compound at the electrode surface during voltammetric measurements. Experience showed that for microelectrodes in the range 0.5 to 30 μm, this thickness should be larger than 20 μm. It can thus be concluded that the gel thickness should be in the range 20 to 5,000 μm. A thickness of a few hundred microns being generally well suited for the usual chemical species.

In accordance with the present invention, the simple microsensor or the ensemble of microsensors, as well as the integrated electrochemical microsystem allow to obviate the prior art disadvantages, by providing a robust sensor suitable for direct analysis in aqueous environment containing the test compound, over long periods of time, with an increased sensitivity. The measure is not altered by the presence of interfering compounds of type 1 or 2. The specificity allows to selectively measure the dissolved forms of the compound to analyse, even when this compound is adsorbed on colloids or particles or incorporated in them. By acidification, the total concentration can be obtained. The microsensor and the integrated electrochemical microsystem allow thus to get without sample handling, an information which classically requires a filtration or ultrafiltration step which is a long and disturbing procedure (modification of the compounds present in the sample, contaminations or losses by adsorption for trace analyses, interferences of type 3).

Unlike for classical electrochemical systems, where there is a salt bridge between the reference electrode and the solution to analyse, in the integrated electrochemical microsystem of the present invention, there is no such a salt bridge separating the reference electrode from the solution of the gel. In classical systems, the contaminations occurring from the bridge constitute an important problem for the analyses of compound in concentration lower than $10^{-8}M$. In the integrated Microsystems of the present invention, contaminations are thus avoided. The equilibration of pressure between the test solution and the solution of the salt bridge classical reference electrode, is also a problem when an electrochemical probe is used for in situ analyses at pressure larger than 1 atmosphere (for example at large depth in the oceans). The present microsystem also allows to avoid this problem.

The possibility of retaining in the gel buffer compounds able to fix the physicochemical conditions has two advantages. First voltammetric measurements can be carried out in the optimal experimental conditions. For example with a pH buffer, the precipitation of metal ions as metal hydroxides can be avoided during the oxygen reduction. Furthermore, in the case of the integrated microsystem, the potential of the reference electrode can be fixed inside the gel because of stable chemical conditions in the gel. For example, the potential of an $Ir/IrO_2$ reference electrode can be fixed by the acid-base buffer also used to eliminate the oxygen interferences.

According to the present invention, the ensemble of microsensors, where the microelectrodes are separately addressable, allows to measure concentration gradients of a chemical compound in situ and without perturbation of the environment to analyse, for example at the water-sediment or water-air interfaces. The microsensor microelectrodes are then arranged in rows over a total length of a few centimetres and spaced by 100 μm for example. The measuring apparatus associated with the sensor includes a multipotentiostat, allowing simultaneous measurements on several electrodes.

BRIEF DESCRIPTION OF THE DRAWINGS

Further descriptions of embodiments of the present invention for a microsensor, an ensemble of microsensors and an integrated microsystem, and examples of measurements obtained with these devices serve to explain the principle of this invention with reference to the accompanying drawings in which :

FIG. 9: microsensor with gel)

DETAILED DESCRIPTIONS OF THE PREFERRED EMBODIMENTS

Figure 1:
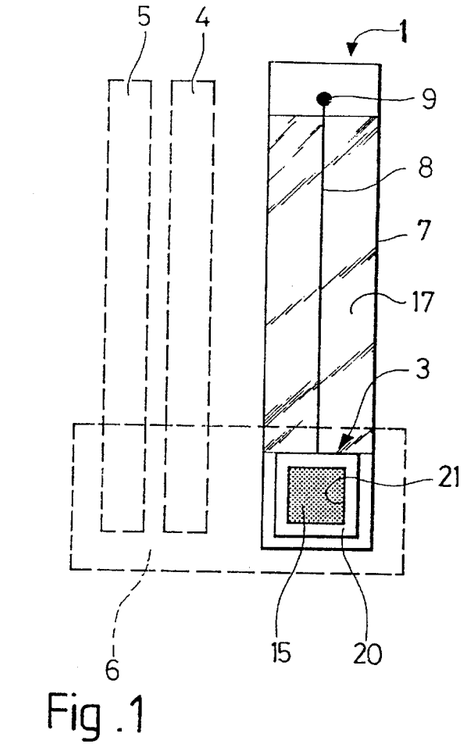
FIG. 1 is a top view of a measuring device including a simple microsensor.
Figure 2:
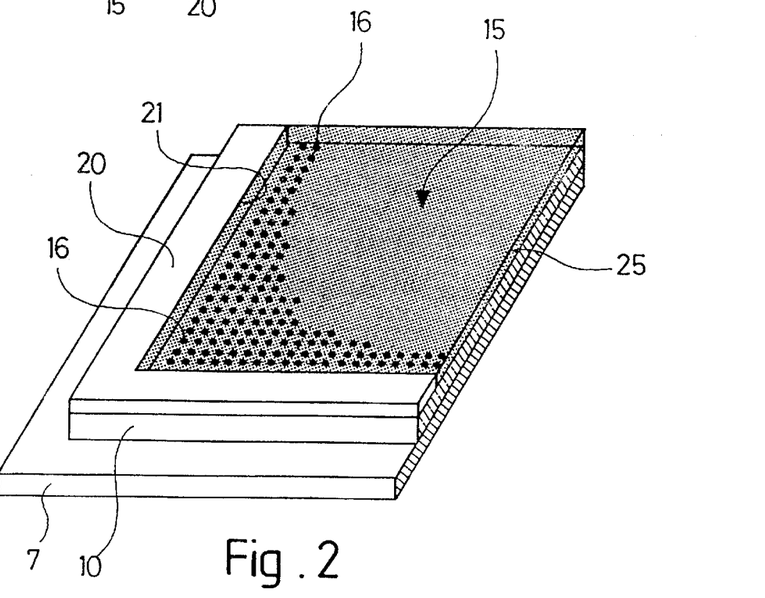
FIG. 2 is a fragmentary schematic perspective view of the microsensor expanded from FIG. 1.
Figure 3:
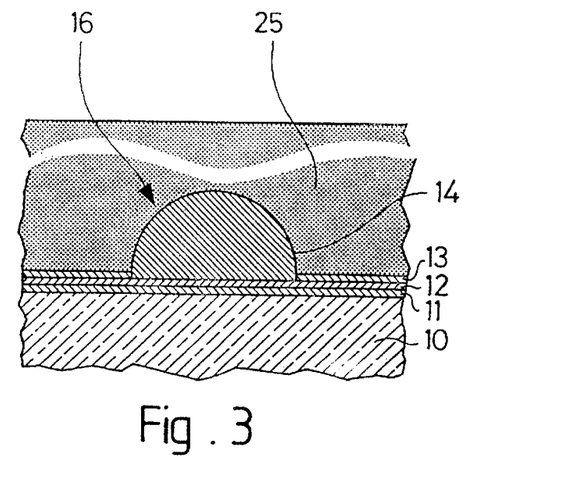
FIG. 3 is an expanded section view of a microsensor shown in FIG. 1 or FIG. 2, taken at the level of a microelectrode diameter.

FIGS. 1 through 3, show a sensor 1 including a simple microsensor 3 which constitutes the working electrode, associated with a classical macro counter electrode 4 and a classical reference electrode 5. The whole set of electrodes forms an electrochemical analytical device 6 which must be dipped in the aqueous environment where the analyse must be carried out. In the example of FIG. 1, the microsensor 3 is supported by a thin isolated oblong substrate 7. The connection with the measuring apparatus (not shown) is done with the contact 9 linked to the microsensor 3 with a conductor 8 protected by an insulating layer 17 covering the substrate 7. The material used for the substrate 7 can be for example Plexiglas or epoxy resin with a thickness of at least 0.1 mm, a length larger than 1 cm and a width larger 1 mm. As will be explained in more details in a second embodiment, the working electrode, the counter electrode and the reference electrode may all be assembled on a single substrate to form an integrated electrochemical microsystem.

Referring now to FIG. 2, it can be seen that the sensor 3 fixed to the substrate 7 is constituted of a chip 10 on which an array 15 of microelectrodes 16 have been structured.

The limits of the array 15 are fixed by the opening 21 of a frame 20, inside which a gel 25 has been deposited. The chip 10 can be a silicon chip of small dimensions (4×4 mm), but other materials (ceramic, glass and plastic materials. . . ) as well as other dimensions can also be used. In this example, the microelectrodes 16 form an interconnected array 15, and one of the electrode is represented on FIG. 3.

Using the well known thin film deposition and photolithography technologies for the fabrication of microstructures, a silicon chip 10 is passivated with a $Si_3N_4$ deposit 11 of thickness varying in the range 1'000 to 2'500 Å (2'000 Å for example). A uniform iridium layer 12 is then deposited with a thickness varying in the range 500 to 2'000 Å (2'000 Å for example), fixed by a layer of tantalum (not shown) with a thickness varying in the range 100 to 200 Å (200 Å for example), on which a $Si_3N_4$ isolating layer 13 is deposited. Openings constituting the microelectrodes 16 are formed by photolithography in the $Si_3N_4$ layer 13. Their diameter is in the range 0.5 to 30 μm and their geometry is variable. In a simple microsensor, where all the microelectrodes are interconnected, the resulting array can be regular and the spacing between the electrodes can be in the range 10 to 500 μm, although other geometries and dimensions can be chosen. The microelectrodes 16 are then cleaned electrochemically in a $10^2$M purified nitric acid by applying a potential of −1900 V for 2 min., and the array 15 can then be coated with a gel 25, as further described.

Depending on the oxidoreduction potential of the chemical species to analyse, each microelectrode can be plated or not, with mercury. This is carried out by electrodeposition through the membrane formed by the gel. A potential in the range −100 to −1'000 mV (typically −400 mV) with respect to a Ag/AgCl/KCl 3M/$NaNO_3$ 0.1M electrode is applied in a solution containing $10^{-1}$ to $10^{-3}$M perchloric acid (typically $10^{-2}$M) and 1 to 100 mM mercuric acetate (typically 5 mM). Base on the well known voltammetric techniques, the shape of the mercury deposit is controlled by the electrodeposition time. For example as can be seen in FIG. 3, an hemispherical deposit 14 can be obtained. The reoxidation of mercury is carried out by scanning the potential typically between −300 and 300 mV at a scan rate of 5 mV.s$^{-1}$, in a degassed 1M potassium thiocyanate solution. When necessary, usually after using the microsensor for more than 10 days, the mercury deposition/reoxidation procedure should be repeated, without modification of the membrane formed by the gel. Experience has shown that the gel is able to sustain numerous mercury regeneration procedures without deterioration. According to the present invention, the life time of the microsensor is at least one year.

Figure 4:
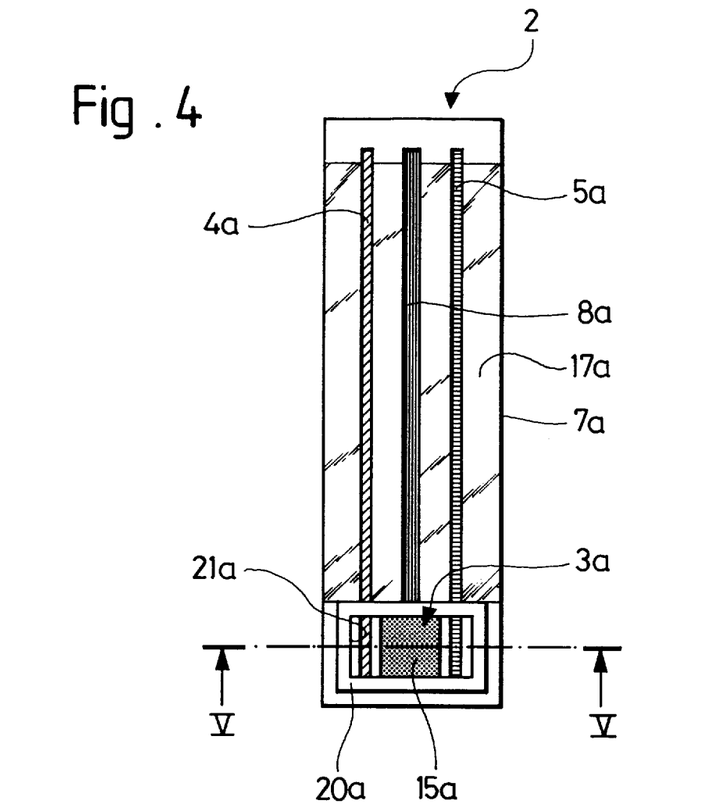
FIG. 4 is a top view of the integrated electrochemical microsystem including an ensemble of microsensors.
Figure 5:
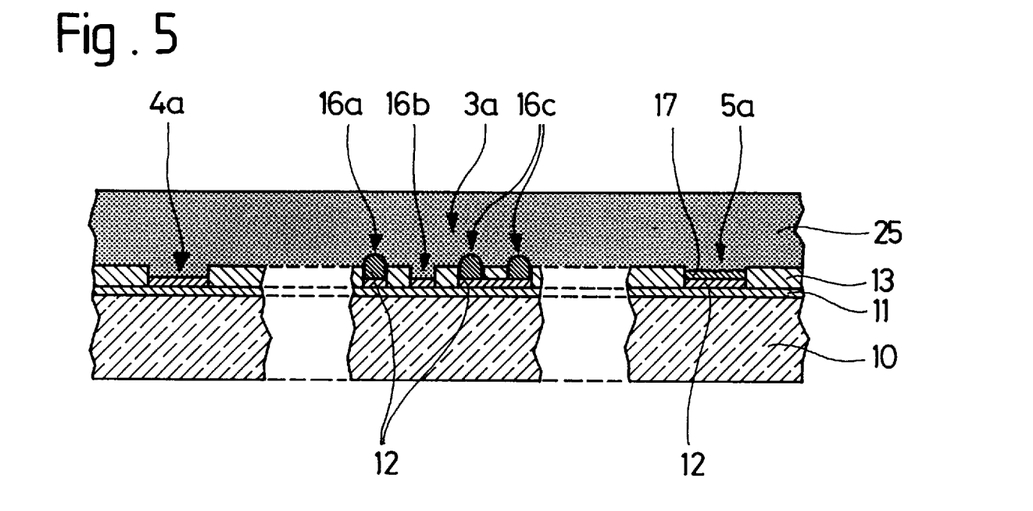
FIG. 5 is an expanded fragmentary section view taken from FIG. 4 along the v—v line.

In FIGS. 4 and 5, is represented an integrated electrochemical microsystem 2, which includes an ensemble of microelectrodes 3a (i.e. a microsensor which is formed by separated mercury plated microelectrodes 16a or non mercury plated microelectrodes 16b), or groups of interconnected microelectrodes 16c. Each microelectrode or group of microelectrodes are electrically isolated and can be separately addressed by means of a network of conductors 8a covered with an insulating layer 17a, or/and by multiplexing.

The geometrical configuration of the microelectrodes on the chip 10 can be most variable. It is possible for example to have a regular array addressed by multiplexing in rows and columns, such as the device described by G. C. Fiaccabrino et al (Sensor and Actuators B, 18–19, 675–677 (1994), Ref. 5). It is also possible to arrange the microelectrodes or the groups of microelectrodes in rows, along the substrate 7 axis, and thus forming an integrated electrochemical microsystem capable of measuring concentration profile of a given chemical compound near the interface of two phases, or in an heterogeneous aqueous system. The fabrication of the microelectrode array is obtained with a procedure analogous to the procedure described in the first mode of fabrication, by thin film deposition and photolithography. An additional intermediary step is the engraving of the iridium layer, either by wet procedure (lift-off), or by dry procedure (plasma). As previously indicated the array is coated with a gel 25. Such an ensemble of microsensors can be used in the device described in the first embodiment, which means with a reference electrode 5 and a separated auxiliary electrode 4. It can also constitutes the working electrode of an integrated electrochemical microsystem. In a simple embodiment, the width of the substrate 7 shown in FIG. 1 can be increased, and the reference electrode 5 and the auxiliary electrode 4a can be placed next to the frame 20a delimiting the microsensors 3a. This can be achieved by lamination or by electrodeposition of the suitable conducting materials. In a preferred embodiment represented in FIG. 4, the frame 20a, covers most of the width of the substrate 7a and its opening 21a liberates the three electrodes 3a, 4a, 5a, which are then totally coated with the gel 25. In this case the gel must contain a chemical compound which maintain the reference electrode potential at a constant value. For example a pH buffer can be used if the reference electrode is made of $Ir/Iro_2$. With reference to the prior art electrochemical sensors, such construction offers the advantage of eliminating junction potential between the reference and the working electrodes and also the contaminations due to the classical reference electrode salt bridge. Reference electrodes others than $Ir/IrO_2$ can also be used.

In a preferred configuration, the three electrodes can be structured in one and the same iridium deposit 12, the microelectrodes being bare iridium 16b or mercury plated iridium 16a, as indicated in the first embodiment. The auxiliary electrode is non coated iridium and the reference electrode is oxidised electrochemically, in a 0.1M sulphuric acid solution, in order to form an iridium oxide deposit 17, and hence the $Ir/IrO_2$ couple.

In the integrated electrochemical system just described, the ensemble of microsensors 3a can also be a simple microsensor 3, as described in the first embodiment, the network of conductors 7a is then reduced to a unique conductor.

EXAMPLES

The gel coating of the microsensor or the integrated electrochemical microsystem (in the frame 20, 20a defined by the opening 21, 21a) as well as the tests carried out with the said analytical devices are described in more details in the following examples.

EXAMPLE 1

Coating with Polyhydroxyethylmetacrylate (polyHEMA)

After having build a microsensor as previously indicated, and before the formation of the gel, a surface pretreatment may be suitable to improve the adhesion of the gel on the said surface. For this purpose, a solution of derived silane methacrylic in toluene can be used. For example a solution of toluene containing 10% of (trimethoxysilyl) propyl methacrylate and 0.5% water heated at 60° C. can be used.

To form the gel, a prepolymeric solution containing 57.5% (weigh/weigh) hydroxyethylmethacrylate (HEMA), 38% ethylene glycol, 1% dimethoxyphenyl-acetophenone, 1% polyvinylpyrolidone and 1% tetraethyleneglycol dimethacrylate can be deposited with a micropipette on the chip supporting the microsensor. The thickness of the membrane to be formed can be controlled either by adjusting the quantity of the prepolymeric solution, or by adjusting the speed of rotation when an horizontal micro centrifuge is used. A Mylar® film is then applied to avoid penetration of oxygen which has the property of inhibiting the polymerisation reaction. Using a standard filter and a standard aligning mask, the prepolymeric composition is exposed to UV light for approximately 30 s to 3 min. This is followed by a development in ethanol.

It is also possible to carry out the polymerisation by mean of chemistry only, using a prepolymeric composition containing 5 ml HEMA, 0.02 ml tetraethyleneglycol dimethacrylate, 50 mg $Na_2S_2O_8$, 100 mg $Na_2S_2O_5$, as redox initiator, 1.25 ml ethylene glycol and 1.25 ml water. The needed quantity of the said composition is deposited in the window 21 of the frame 20, and the polymerisation is carried out for 48 h at room temperature.

The obtained polymer is then hydratable to a level larger than 70%. It can also be noticed that the frame 20 is not necessary when the polymerisation is carried out under UV light.

EXAMPLE 2

Polyacrylamide gel formation

A gel of the chosen thickness is obtained by proceeding as indicated in example 1, but the prepolymeric composition now contains 30% (w/w) acrylamide, 5% N, N'-methylene diacrylamide, 0.1 mg/ml riboflavine phosphate, 2 µl/ml N, N, N', N'-tetramethyl ethylenediamine in a glycerin buffer solution (in a proportion between 1/1 and 1/3 ). The prepolymeric composition is exposed under UV light for approximately 1–10 min, and the development is carried out with water.

It is also possible to carry out the polymerisation by mean of chemistry only, using for example a prepolymeric composition containing acrylamide and bisacrylamide with ammonium persulphate as initiator and tetramethyl ethylenediamine (TEMED) as catalyst. The solution is immediately placed on the sensor and left for approximately 45 min at 40° C.

EXAMPLE 3

Agarose gel formation

To produce a gel having the required mechanical resistance and chemical qualities, a very pure agarose must be used. In particular, its content in sulphate groups must be less than 0.3%, and preferably below 0.03%. The mechanical resistance being defined as the pressure necessary to break the gel, a mechanical resistance adapted for the sensor of the present invention should be larger than 500 $g/cm^2$, preferably in the order of 2'000 $g/cm^2$. The experience has shown that for different types of agarose, an aqueous gel containing 1 to 5% of agarose fulfil the requirement concerning the mechanical resistance. Such a gel also have the suited hydration and porosity, which provides good fabrication reproducibility and therefore good reliability for the measurements carried out with the said microsensors.

To prepare the gel, distilled water is heated in a 80° C. water bath, and the desired quantity of agarose (for example 1.5%) is added under vigorous stirring. The solution is then gently brought to boil for approximately 10 min, until dissolution of the agarose. The heating is then stopped, and the solution is left in the water bath until complete elimination of the bubbles. The quantity of solution corresponding to the desired thickness of gel is then deposited with a micropipette in the window 21 of the frame 20. To produce a flat film a Mylar® film is applied to press the gel, or an horizontal micro centrifuge can be used. The gel must then be cooled at room temperature for a few minutes. As indicated in example 1, the surface where the gel is deposited can also be pretreated. When a pH buffered gel is needed, a buffer compound is added to the distilled water used to produce the gel. For a system buffered at pH 7–8, for example for measurements in tap water, a 10–2M HEPES buffer can be used.

An agarose gel is thus produced which has a constant volume, and which is unaffected by the physicochemical properties of the aqueous solution to analyses.

EXAMPLE 4

Influence of stirring on the diffusion in agarose gel

The following experimentation shows the efficiency of the sensor gel to eliminate the influence of stirring the medium to analyse, on the measured signals. With the prior art sensors, irreproducible signals are observed due to this effect. The sensor used here is a simple mercury plated microsensor with diameter in the range 6.3 to 7.6 $\mu$m, coated with a 1.5% agarose gel of thickness 800 to 850 $\mu$m. The test solution contains 9.6 $\mu$M Pb(II). The voltammetric technique used was SWCSV with an initial potential of −100 mV, a final potential of −1'100 mV, a pulse amplitude of 25 mV, a step amplitude of 4 mV and a frequency of 50 Hz.

Figure 6:
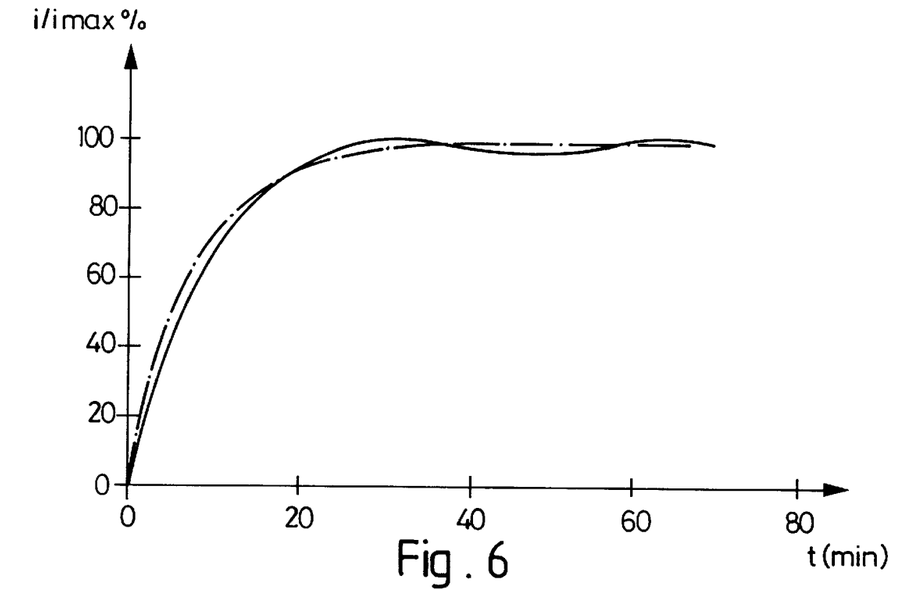
FIG. 6 is a graph showing the diffusion of a compound though the gel, with or without stirring.

FIG. 6 shows the Pb(II) reduction current during its diffusion in the gel, for an agitated solution (full line curve) and a quiescent solution (dotted line curve). The two recorded curves virtually merging together, this experiment clearly shows the efficiency of the gel as a protection against solution stirring effects on the analytical signals.

EXAMPLE 5

Reproducibility and sensitivity limits of an agarose gel microsensor

Figure 7:
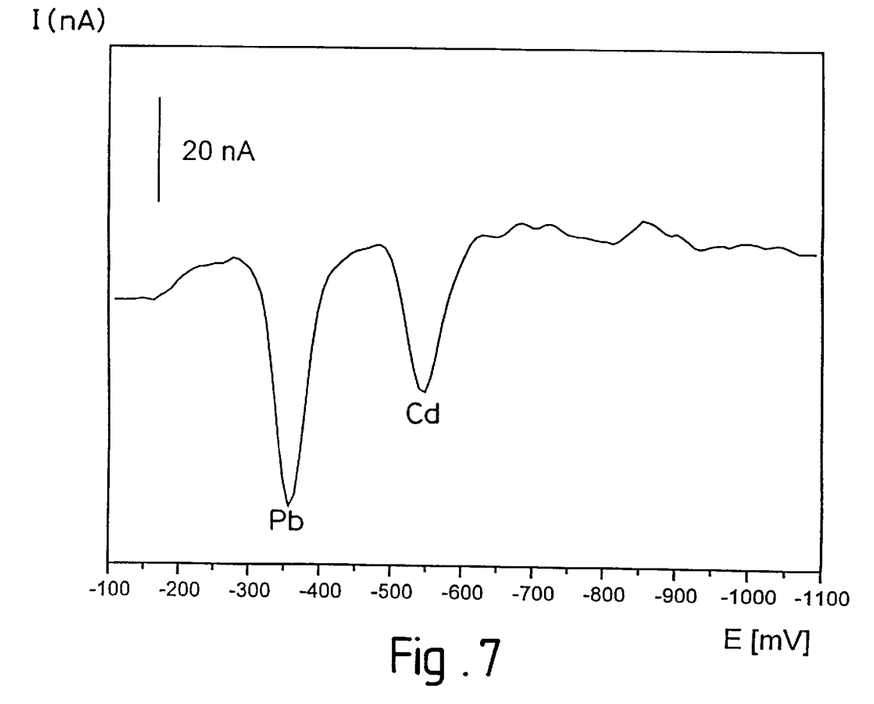
FIG. 7 is a graph showing measurements of Pb and Cd in an aqueous solution.

FIG. 7 shows a characteristic voltammogram obtained by square wave anodic stripping voltammetry (SWASV), with a degassed solution of 9.6 nM Pb(II), 8.9 nM Cd(II) in 0.1M NaNO$_3$ buffered at pH 4. The experiment was carried out with a mercury plated microsensor coated with a 1.5% agarose gel of thickness 800 $\mu$m. The experimental conditions were: electrodeposition and initial potential −1'100 mV; electrodeposition time 1 min; final potential −100 mV; pulse amplitude 25 mV; step amplitude 8 mV; frequency 50 Hz. In these conditions a very good reproducibility is obtained when the experiment is repeated for a period of 5 to 6 hours, with a standard deviation in the order of 4% for both Pb(II) and Cd(II). With a preconcentration time of 15 min, a sensitivity as small as 50 pM can be obtained for both metals, with peak intensities larger than twice the amplitude of the noise level. Similar sensitivity was obtained with a microsensor without agarose gel, it can thus be concluded that the presence of an agarose gel on the microelectrodes does not affect the performance of the microsensor. Further more it should be noticed that the sensitivity of the present microsensors is largely increased compared to bare microsensor presented in Ref. 3.

EXAMPLE 6

Agarose gel efficiency for the protection against interfering species of type 2

Figure 8:
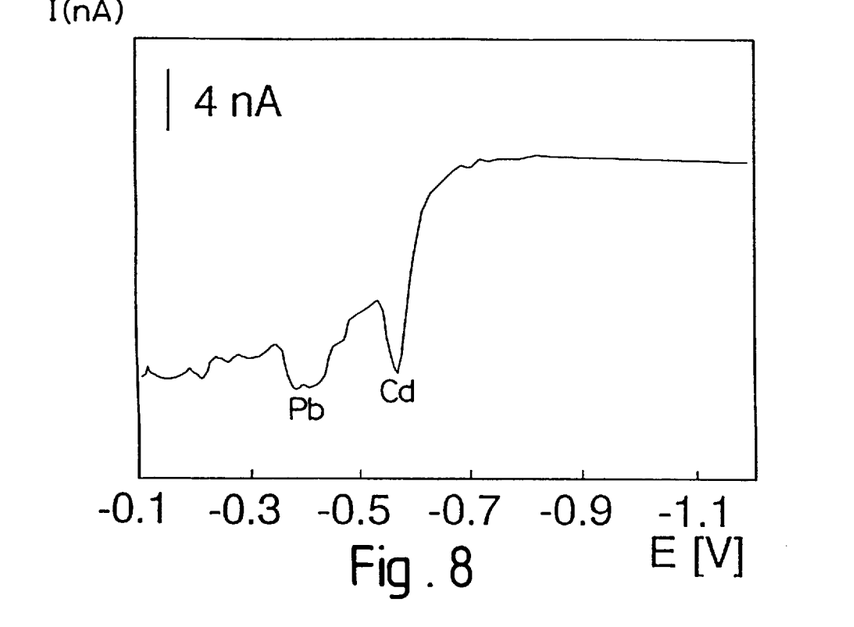
FIGS. 8 and 9 show the influence of the gel when interfering species of type 2 are present (FIG. 8: microsensor without the gel.
Figure 9:
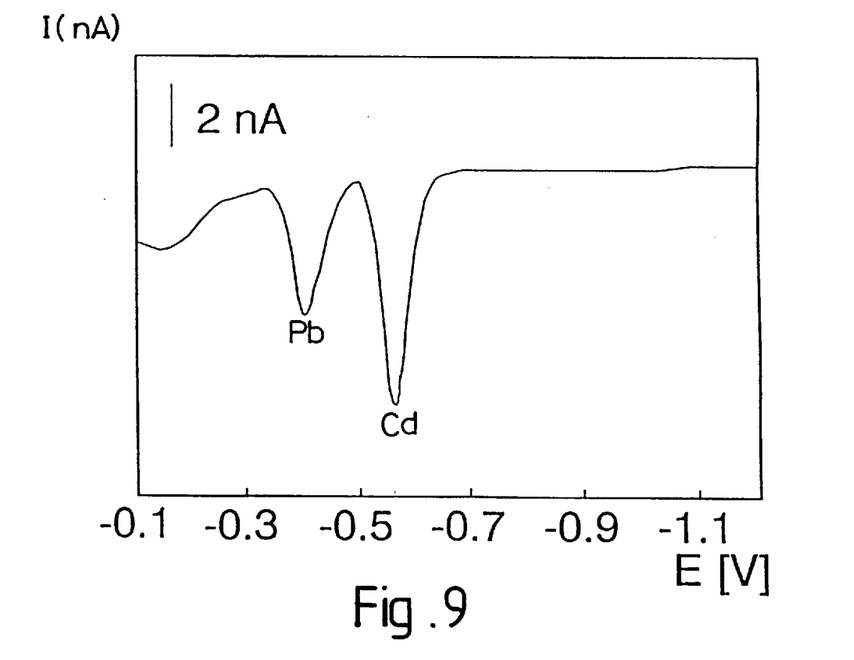

To a solution of 0.1M NaNO$_3$ and 10$^{-2}$M MES buffer (pH 6.7) containing 46 nM Pb(II) 42 nM Cd(II) was added 32 mg/l fulvic acids, which is a concentration much larger than that found in typical natural waters. SWASV measurements were then carried out in the same conditions as in example 5 with a microsensor without agarose gel (FIG. 8) and with gel as described in the present invention (FIG. 9). The comparison of the two figures clearly shows the positive influence of the gel on the sensor disclosed in the present invention.

These results were confirmed by field analyses, where the concentration of Pb(II) was measured in river water (Arve-Geneva Switzerland), at four different sampling dates, with a microsensor without gel and with a microsensor with a 1.5% agarose gel as disclosed in the present invention. Measurements were carried out in raw waters and in waters after filtration with a membrane porosity of 0.2 $\mu$m. Results are reported in the following table:

| sample number | Microsensor type | Dissolved Pb (II) concentration (nM) | |
|---|---|---|---|
| | | raw water | 0.2 $\mu$m filtrated water |
| 1 | without gel | 0.21 | 0.96 |
| 2 | without gel | 0.57 | 0.73 |
| 3 | with gel | 0.70 | 0.62 |
| 4 | with gel | 1.00 | 1.07 |

The comparison of the analyses carried out in the raw and filtrated waters, with the microsensor without gel shows that the results obtained are too low for the raw samples. This is due to interferences of colloids in suspensions (whose concentration has varied from 30 to 70 mg/l between experiment 1 to 4). In contrast, it can be seen that the presence of colloids has virtually no influence on the analyses carried out with the gel coated microsensor disclosed in the present invention. In this case the filtration step is therefore not necessary. Finally it should be noticed that extremely small concentrations can be determined with an error of 6%.

EXAMPLE 7

Direct selective detection of dissolved forms and total concentrations of Pb(II) and Cd(II)

Figure 10:
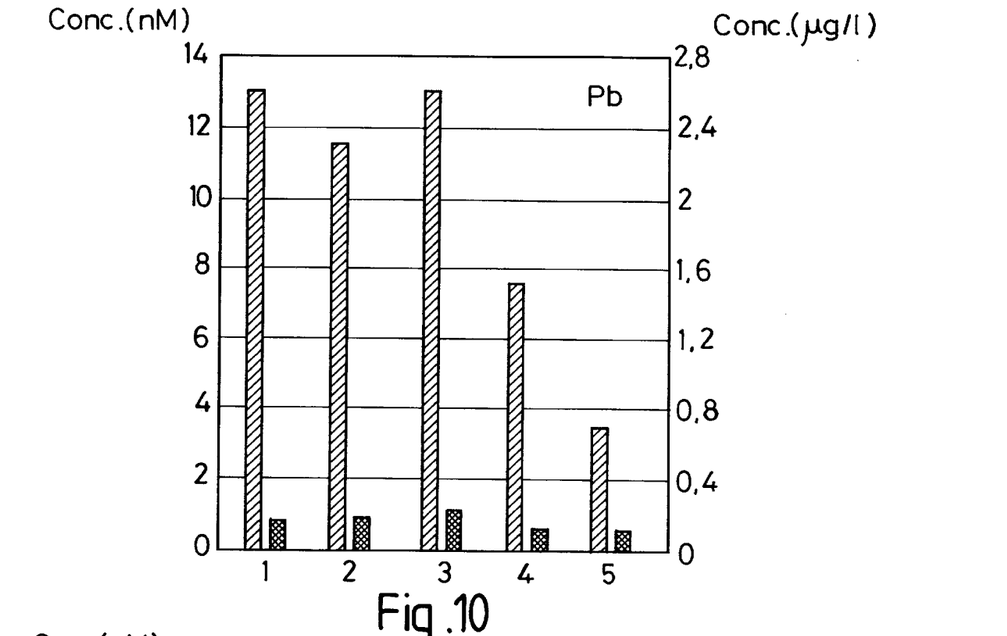
FIGS. 10 and 11 represent diagrams for the analysis of the dissolved forms (bars with crosses) of Pb(II) and Cd(II) and their total concentrations (hatched bars), directly in river.
Figure 11:
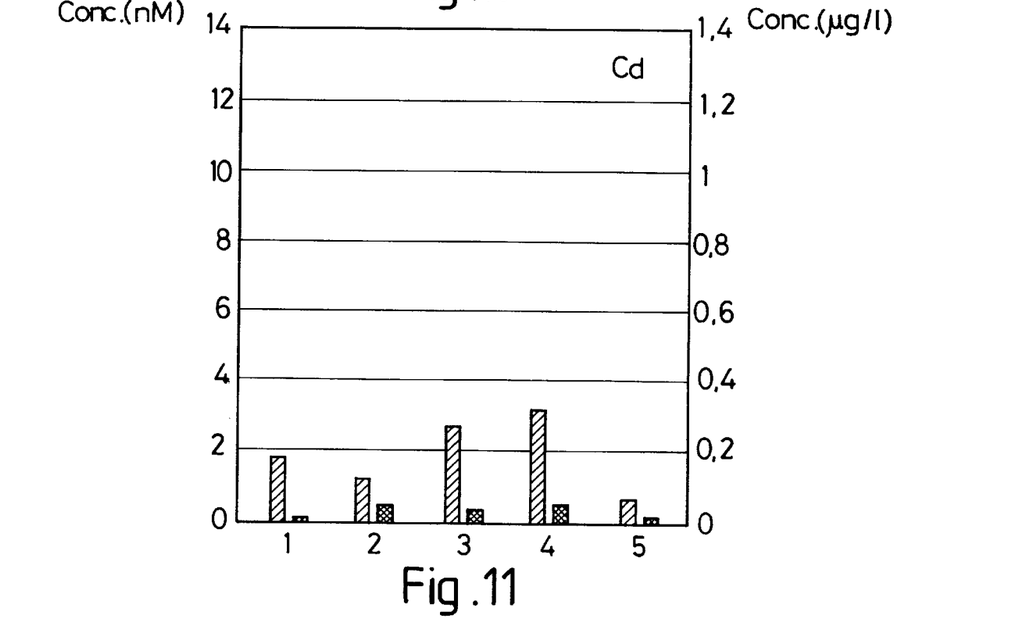

Samples of river water (Arve) have been sampled at five different dates, and the concentration of Pb(II) (FIG. 10) and Cd(II) (FIG. 11) have been measured with the SWASV method previously described. The samples were either analysed directly without sample pretreatment (diagram with crosspieces), or they were acidified with 10$^-$M HNO$_3$ and stored for two days at 4° C. in the dark to allow the complete desorption of the metal adsorbed on the particles in suspension (diagram with hatching). The diagrams with crosspieces represent the concentrations of the dissolved forms (size<3–5 nm) and the diagrams with hatchings represent the total concentrations. The difference between the diagrams with hatchings and those with crosspieces represents the concentration of the particulate plus colloidal forms of the metals. The measurement variations between the different samples correspond to natural variations. For the five samples, the average dissolved fractions of Pb(II) and Cd(II) represent respectively 9±1.5% and 14±2.8% of the total. The great sensitivity of the method can also be noticed, the smallest measured cadmium concentration being 50 pM (5.5 ng/l), with an accuracy of 8% for concentration below 1 nM.

According to the present invention, a microsensor or an integrated electrochemical microsensor, where the microelectrodes either interconnected or not, are coated with an hydrophilic gel, constitutes therefore a novel and non obvious system for those skilled in the art. The compound to analyse is equilibrated by dialysis between the system to analyse and the gel, hence allowing the analysis of the said compound inside the gel, where the physicochemical conditions can be controlled and adjust to increase the reliability, sensitivity and reproducibility of the analyses.

What is claimed is:

1. A microsensor for voltametric techniques allowing the measurement of concentration of at least one chemical compound with small molecular weight under organic, inorganic, neutral or ionic form, in complex aqueous environment, said microsensor comprising an array of microelectrodes, assembled on a chip supported by an isolating substrate, and linked to a contact allowing the connection to a measuring apparatus with at least one conductor protected by an isolating layer, wherein said microsensor is totally coated with an hydrophilic gel which is chemically inert with respect to the chemical compound, is hydrated at a level of at least 70%, and has a thickness in the range of 50 µm to 5,000 µm representing at least 10 times the diameter of the microelectrodes, said diameter ranging from 0.5 to 30 µm, and said gel is a screen against interfering macromolecular or colloidal compounds as against hydrodynamic flux.

2. A microsensor as claimed in claim 1, wherein the microelectrode are interconnected to form a simple microsensor.

3. A microsensor as claimed in claim 1, wherein the microelectrodes as individuals or as groups, are electrically isolated from each other and separately addressable to form an ensemble of microsensors allowing the determination of concentration gradients in heterogeneous systems, or the determination of concentration of several different compounds by applying different electrochemical conditions on respective microelectrodes.

4. A microsensor as claimed in claim 1, wherein the microelectrodes are obtained by thin film deposition and photolithography, from a conducting layer of iridium.

5. A microsensor as claimed in claim 4, wherein at least one of the microelectrodes is plated with a mercury layer by electrode position from a mercury salt solution through the hydrophilic gel coating the microsensor.

6. A microsensor as claimed in claim 5, wherein the mercury deposit has the shape of a film or a part of sphere, the said shape being controlled by the time of electrodeposition.

7. A microsensor as claimed in claim 1, wherein the array of microelectrodes is fixed by the opening of a frame fixed onto the substrate.

8. A microsensor as claimed in claim 1, wherein the hydrophilic gel has a high mechanical resistance, a porosity and diffusional characteristics allowing the diffusion of the chemical compound to be analyzed while forming a barrier for the macromolecular or colloidal compounds.

9. A microsensor as claimed in claim 1, wherein the hydrophilic gel has an intrinsic structure without any neutral or charged complexing sites for the chemical compound to be analyzed, but with binding groups for constituents contributing in maintaining the optimal physicochemical conditions in the gel.

10. A microsensor as claimed in claim 1, wherein the hydrophilic gel incorporates a buffer for fixing the pH value inside the gel, the buffer being chosen from the group of buffers consisting of MES, PIPES, cholamine chloride, HEPES, HEPPS, HEPPSO, MOPS and MOPSO buffers.

11. A microsensor as claimed in claim 10, wherein the hydrophilic gel has a porosity high enough to allow the diffusion of the compound to be analyzed, but low enough to retain by their size particles on which are fixed the buffers maintaining the physicochemical conditions stable in the gel.

12. A microsensor as claimed in claim 1, wherein the hydrophilic gel is obtained from a compound chosen from a group consisting of cellulose and cellulose derivatives, reticulated dextrans, purified agarose with low content in sulphate or carbonyl groups, reticulated agarose, polyacrylamide, polyacrylamide and agarose polymers, and hydroxy alkylmethacrylate.

13. A microsensor as claimed in claim 12, wherein the hydrophilic gel is made of agarose in a proportion of 1 to 5%, and has a constant volume independent of the time and of the physicochemical properties of the aqueous environment where the measurements are carried out.

14. A microsensor as claimed in claim 1, wherein the hydrophilic gel has a thickness in the range of 200 to 900 µm.

15. An integrated electrochemical microsystem for an electrochemical analysis device for determining, in an aqueous environment, the concentration or the concentration gradient of at least one chemical compound having a molecular mass less than 1,000, under organic, inorganic, neutral or ionic form, including a working electrode and a reference electrode wherein the working electrode is a microsensor, as claimed in claim 1, and wherei n the w orking and reference electrodes are supported on a single isolated substrate, and are both coated with said hydrophilic gel.

16. An integrated electrochemical microsystem as claimed in claim 15, and further comprising an auxiliary electrode wherein the reference electrode is a $Ir/IrO_2$ electrode and the auxiliary electrode is a Ir electrode, the reference and auxiliary electrodes being disposed on said substrate.

17. A microsensor as claimed in claim 1 wherein the microelectrodes comprise thin films of iridium.

18. A microsensor as claimed in claim 17 wherein at least one of the microelectrodes comprises a mercury layer covering the iridium thin film.

19. A microsensor as claimed in claim 18 wherein said mercury layer is a thin film.

20. A microsensor as claimed in claim 18 wherein said mercury layer has a part-spherical shape.

* * * * *